(12) United States Patent
Wilson et al.

(10) Patent No.: US 9,355,214 B2
(45) Date of Patent: May 31, 2016

(54) FALSE CLINICAL ALARM RATE REDUCTION

(71) Applicants: Jason Wilson, Toronto (CA); Robert Jeff Frank, Baltimore, MD (US)

(72) Inventors: Jason Wilson, Toronto (CA); Robert Jeff Frank, Baltimore, MD (US)

(73) Assignee: Globe Star, Inc., Toronto (CA)

( * ) Notice: Subject to any disclaimer, the term of this patent is extended or adjusted under 35 U.S.C. 154(b) by 257 days.

(21) Appl. No.: 14/304,640

(22) Filed: Jun. 13, 2014

(65) Prior Publication Data

US 2015/0254957 A1 Sep. 10, 2015

Related U.S. Application Data

(60) Provisional application No. 61/949,287, filed on Mar. 7, 2014.

(51) Int. Cl.
| | |
|---|---|
| G08C 19/00 | (2006.01) |
| G08B 21/00 | (2006.01) |
| G08C 19/16 | (2006.01) |
| A61B 5/04 | (2006.01) |
| A61H 1/00 | (2006.01) |
| A61B 17/00 | (2006.01) |
| G06F 19/00 | (2011.01) |
| A61B 5/00 | (2006.01) |

(52) U.S. Cl.
CPC .............. *G06F 19/34* (2013.01); *G06F 19/345* (2013.01); *A61B 5/746* (2013.01)

(58) Field of Classification Search
USPC .......... 340/679, 506, 508, 573.1, 12.54, 521, 340/500, 539.1, 815.43, 540, 517, 515; 705/3; 600/509; 601/48; 606/65–67, 606/202; 607/18–19
See application file for complete search history.

(56) References Cited

U.S. PATENT DOCUMENTS

| | | | | |
|---|---|---|---|---|
| 2007/0213599 | A1* | 9/2007 | Siejko | A61B 5/00 600/300 |
| 2010/0265073 | A1* | 10/2010 | Harper | A61B 5/0031 340/573.1 |
| 2012/0029314 | A1* | 2/2012 | Paquet | A61B 5/02055 600/301 |
| 2012/0172730 | A1* | 7/2012 | Delos | A61B 5/0205 600/484 |
| 2013/0045685 | A1* | 2/2013 | Kiani | G08B 21/24 455/41.2 |
| 2014/0135588 | A1* | 5/2014 | Al-Ali | G06F 19/327 600/300 |

* cited by examiner

*Primary Examiner* — George Bugg
*Assistant Examiner* — Munear Akki
(74) *Attorney, Agent, or Firm* — Robert Schuler

(57) ABSTRACT

A clinical facility communication network connects a notification system to a plurality of patient monitors and to a plurality of clinician communication devices. Each of the patient monitors operate to detect physiological characteristics associated with a patient and to send event messages to the notification system. The notification system operates to receive the event messages and to determine which of the event messages include information of sufficient clinical significance to warrant generating and sending an alarm to a clinician. The event messages that are determine not to include clinically significant information are ignored.

17 Claims, 5 Drawing Sheets

NETWORK 100

FALSE CLINICAL ALARM RATE REDUCTION

CROSS REFERENCE TO RELATED APPLICATIONS

This application claims the benefit under 35 U.S.C. §119 (e) of U.S. Provisional Patent Application Ser. No. 61/949,287 entitled "FALSE CLINICAL ALARM RATE REDUCTION", filed Mar. 7, 2014, the entire contents of which is incorporated by reference.

BACKGROUND

1. Field of the Invention

The present disclosure relates to a process for identifying short duration, transitory patient events and suspending alarms that are otherwise sent to clinicians.

2. Background

Healthcare organizations place a high value on the collection of real-time physiological parametric information about patients. Such parametric information can include, among other things, a patient's heart rate or other heart function, blood pressure, blood oxygen level, and respiratory rate. This parametric information is typically detected by sensors, attached to a patient, and the sensors transmit the detected physiological information over a wired or wireless link to a patient monitoring device which can in turn be in communication with a local network maintained by the healthcare organization. Subsequent to collecting patient parametric information, a monitor can analyze the information for the purpose of generating and sending alarms to clinicians alerting them to a patient's condition or event, which can be for example a low heart rate or low blood pressure condition. In order for a monitor to determine whether or not an alarm should be generated, a threshold value associated with each physiological parameter can be set. For example, if it is clinically determined that an alarm should be generated when a patient heart rate falls below eighty beats per minute, then the threshold value for recognizing a low heart rate can be set to eighty.

Some events detected by patient monitors can persist for a clinically significant period of time and should always cause an alarm to be generated. Other events only persist for a clinically insignificant period of time (short duration events), and typically, clinicians do not want to be notified each time a short duration event is detected as this type of event is generally considered to be a false indication of a patient's medical condition. A condition referred to as clinician alarm fatigue can occur in the case that a relatively large number of short duration events cause a monitor to generate and send a correspondingly large number of alarms. To the extent that alarm fatigue is a problem, at time a clinician may not respond to an alarm that is not false. This behavior places a patient's health at risk.

One technique that is employed to resolve the problem of alarm fatigue, is to adjust monitor threshold values so that the monitor detects fewer events. For instance, low heart rate threshold can be set to a lower value (75 instead of 80 bpm for instance) such that an event is only detected if a patient's heart rate falls below seventy five beats per minute. Another technique that is used to prevent nuisance alarms is to suspend alarms that are generated due to short duration events. That is, if an event is active for less than a specified period of time (suspend time period), the monitor can cancel the event and not generate an alarm. Yet another solution to this problem is to tie the generation of an alarm to multiple different types of events (heart rate and blood pressure for instance). So, if a patient's heart rate is detected to fall below a threshold value (even for a short period of time) and at substantially the same time their blood pressure also falls below a threshold value, then the monitor can generate and send an alarm. It was found that making the generation of an alarm contingent on to related, but different types of events occurring at substantially the same time reduces the number of nuisance alarms generated by a monitor.

BRIEF DESCRIPTION OF THE DRAWINGS

The present invention can be best understood by reading the specification with reference to the following figures, in which.

DETAILED DESCRIPTION

While suppressing an alarm as the result of a short duration event does reduce the number of nuisance alarms, a succession of these nuisance or short duration events can be indicative of a clinically significant condition that should be reported. Accordingly, a notification system can be designed to both suppress an alarm that is otherwise generated as the result of detecting a short duration event, and at the same time is capable of generating a single alarm to report a plurality of short duration events that occur during a specified period of time. The specified period of time is referred to herein as an event count period, and this period is of a specified, programmable duration, which can be some number of seconds for instance. An event counter operates to count a number of events that are detected during the event count period, and a single alarm is generated if the number of events counted during this event count period is equal to or greater than a selected count threshold value (integer value). During the event count period, an alarm suppression function operates to actively prevent the generation of alarms, and when an event count is detected to be equal to or greater than the count threshold, the alarm suppression function is overridden and an alarm is generated that is transmitted to a clinician, notifying them to a clinically significant event associated with a particular patient. The operation of this notification system within a healthcare setting will now be described with reference to FIG. 1.

Figure 1:
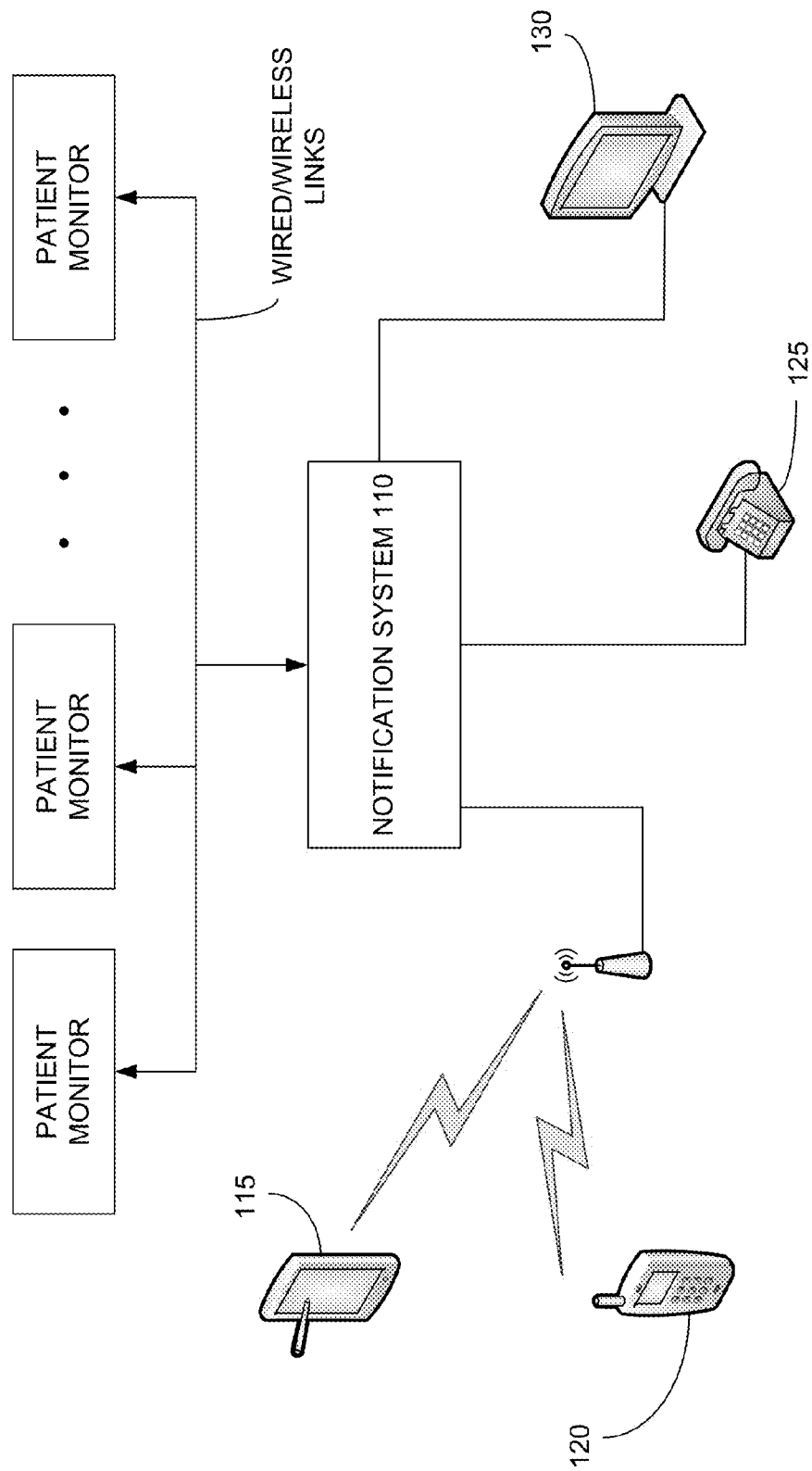
FIG. 1 illustrates a local network configured for a clinical environment.

A patient monitoring and event notification network 100 is illustrated in FIG. 1 that is configured to support the detection of patient related clinical events and to report these events to the appropriate clinical staff. The network 100 is comprised of a plurality of patient monitor devices, a notification system (NS) 110, and a plurality of different types of communication devices 115, 120, 125 and 130 which are in communication with the NS 110 over either wired or wireless mediums. Each patient monitor can receive information from one or more sensors that operate to detect physiological or clinical information relating to a patient. As described earlier, this clinical information can include, but is not limited to heart rate, blood pressure, respiratory rate, blood oxygen, body temperature, and other information. Clinical information detected at each sensor is transmitted to a patient monitor which generally operates to identify clinically significant events that can be reported to the appropriate member(s) of a clinical staff. Typically, a patient monitor is configured to determine whether an event is clinically significant and should be reported, and if so, sends an alarm to a central alarm monitoring station that can be strategically positioned in a clinical facility. However, some or all of the patient monitors in FIG. 1 are configured to send patient event information to the notification system 110, which generally operates to receive the patient event information, determine whether an event is clinically important and can or should be reported, and then generate an alarm that is sent to the appropriate clinician(s).

As described earlier, and according to an embodiment of the invention, the notification system 110 operates to determine whether or not an event is of short duration, and so clinically insignificant, or is of a duration that is considered to be clinically significant. The notification system can be implemented in any suitable network server device that is configured/designed to operate in a clinical communication network setting. The server comprises network interface functionality, storage on optical disk for instance, and volatile and non-volatile memory, such as but not limited to Flash memory, RAM or DRAM, SRAM PROM, ROM, EPOM, EEPROM, and processing means that together support functionality comprising the notification system 110. The system 110 has specially designed functionality that counts and stores the number of each particular type of short duration event, and if the value of the stored count for any particular type of short duration event is determined to be equal to or greater than a selected event threshold count value within a programmed period of time (count period duration), then an alarm is generated and sent to the appropriate clinician(s). However, if a short duration event count does not equal or surpass the selected event threshold count value within the programmed count period duration, then the currently stored count value for the event type is deleted from the store. In the event that the notification system 110 determines that an event is clinically significant, or it determines that a series of short duration events are clinically significant, it operates to generate and send an alarm, and this alarm can be sent to a wireless communication device (such as the tablet device 115 and/or the smart phone 120), and/or the alarm can also be sent to a wired communication device such as the phone 125 or the nurse call station 130. Functionality comprising the notification system 110 that implements the embodiment described above is shown and described with reference to FIG. 2.

Figure 2:
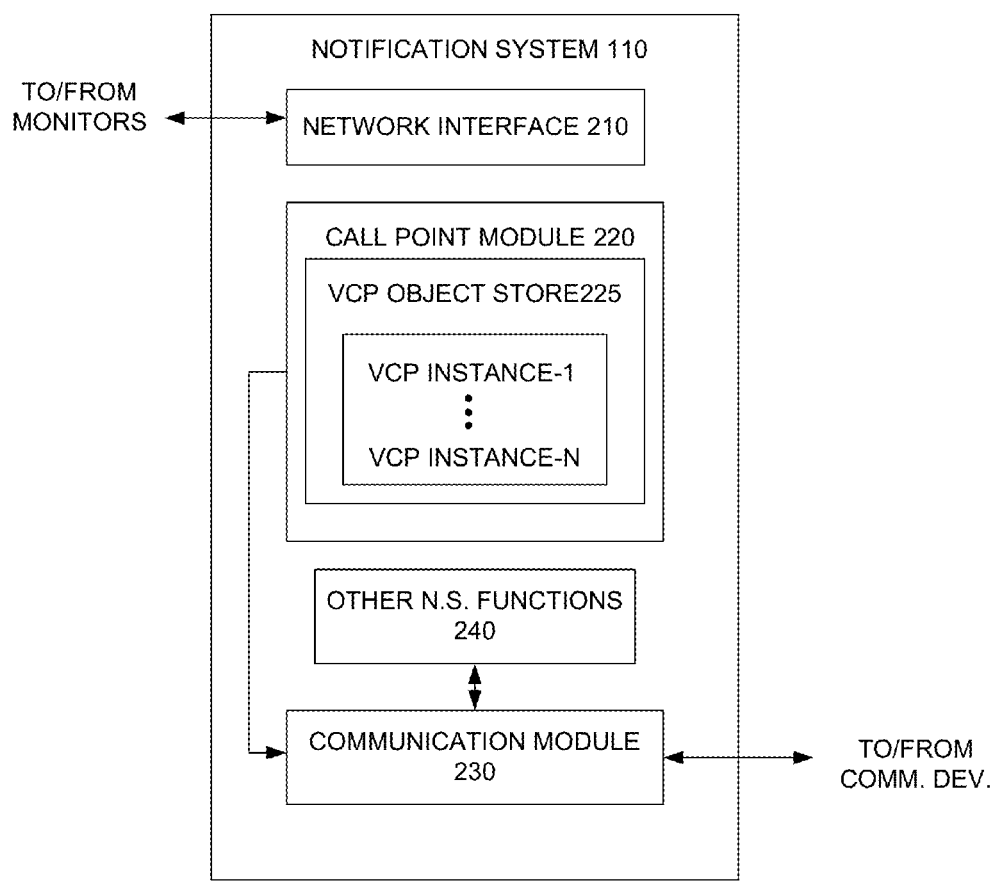
FIG. 2 shows functional elements comprising a notification system that is connected to the network in FIG. 1.

The notification system 110 illustrated in FIG. 2 has a number of different functional modules. It has one or more network interface means 210, it has a virtual call point module 220, it has a communication module 230 and it has other functionality 240. The communication interface means can be implemented as wireless or wired clients. These clients can operate to receive information associated with clinical events from each of the patient monitors, and place this information into a format that can be used by the notification system, or they can operate to place information generated by the notification system into a format that can be sent over the network to the patient monitors. The notification system can be comprised of one or more of these interface clients, and each client is typically linked to only one patient monitor, but alternatively can be linked to more than one monitor. The notification system 110 has a communication module 230 that generally operates to send alarm messages to clinician communication devices and to receive responses from the clinicians to the alarm messages and it has other functionality that performs operations not related to the present invention.

The virtual call point module 220 maintains a store 225 of virtual call point (VCP) instances or objects, VCP Instance-1 to VCP Instance-N, each of which has functionality that operates to implement an embodiment of the invention. According to one embodiment, each VCP instance is dedicated to receiving one type of event information (a type of event information can be any one of a blood pressure, heart rate, body temperature, blood oxygen, etc.) from a single patient, but other VCP instance embodiments can be designed to receive multiple different types of event information from one or more monitors that are associated with a single or more than one patient monitor. A functionality comprising a single instance of a VCP object 300 is illustrated and described with reference to FIG. 3.

Figure 3:
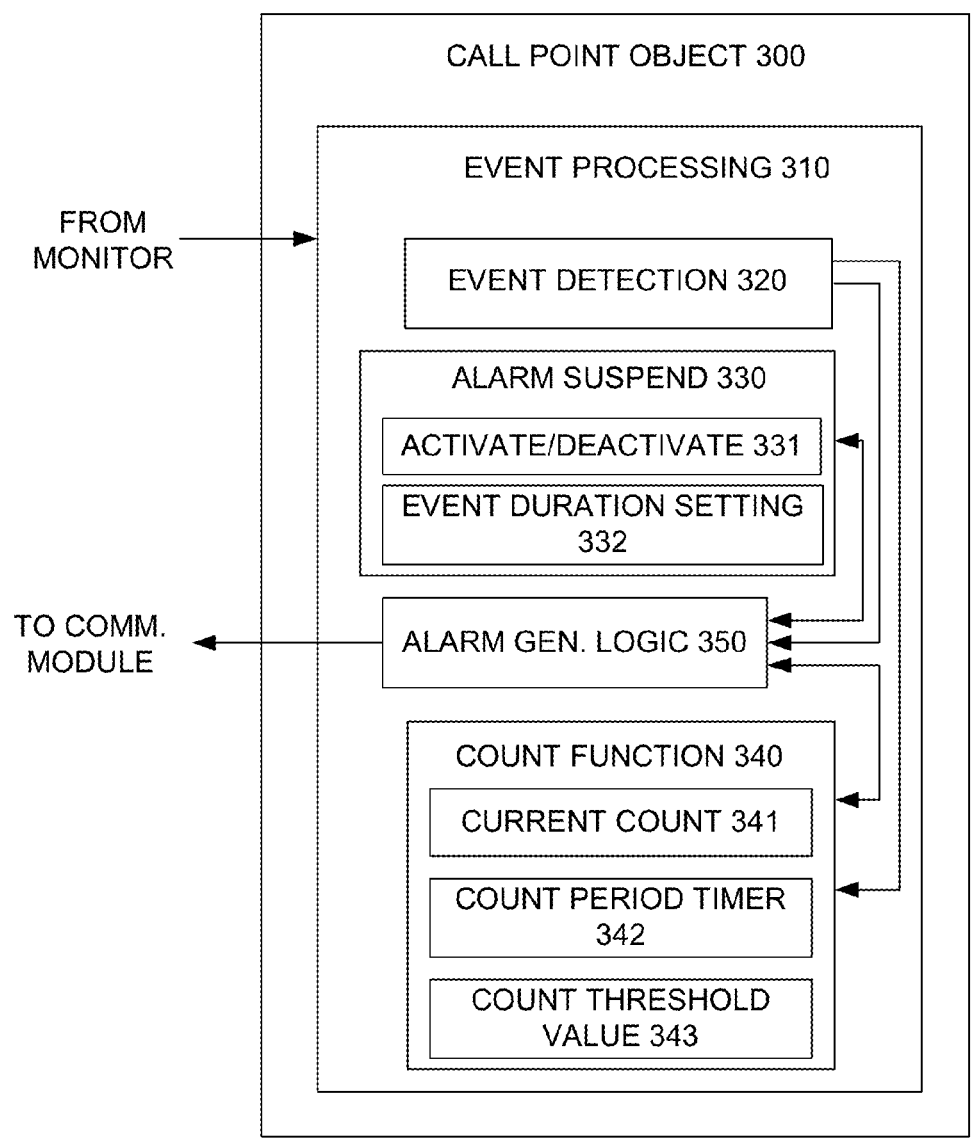
FIG. 3 shows a call point instance that comprises the notification system.

The VCP object 300 in FIG. 3 is comprised of an event processing module 310 that generally operates to detect events and determine whether the detected events are of sufficient significance to warrant notifying a clinician. The event processing module 310 has an clinical event detection function 320, an alarm suspension function 330, a clinical event counting function 340 and alarm generation logic 350. Each event that is detected at a patient monitor causes the monitor to generate an event message that, among other things, is comprised of one or more values associated with a physiological characteristic relating to the event (BP, HR, etc). The event detection function 320 operates to receive an event message from a patient monitor and to parse this information in order to determine a value that is associated with the event, such as the value of a physiological characteristic (heart rate value, blood pressure values . . . i.e., systolic and diastolic BP, etc.) that caused the event information to be sent to the notification system by the monitor. The detection function 320 also detects the time an event message is received or becomes active, and it detects the time that an event message stops being active (becomes inactive). All of this information is stored in memory (not shown) that is associated with the notification system, and can be employed by the alarm generation logic to determine whether or not an alarm should be generated.

The alarm generation logic 350 is comprised of computer instructions, stored in non-volatile memory on a network server or other suitable network computational device, that are operated on by a processor in order to determine if and when an alarm is generated and sent by the notification system 110 to a clinician. As described in more detail later with reference to FIGS. 4a and 4b, the logic 350 employs information generated by the alarm suspend function 330, the event detection function 320, and the count function 340 to determine whether or not a clinical event associated with a patient is significant or not. If the event is determined by the logic to be clinically significant, then an alarm is generated, otherwise an alarm is not generated.

The alarm suspend function 330 generally operates to deactivate or override the logic 350 for the purpose of preventing the generation of an alarm by the notification system 110 in the event that a patient event is not determined to be clinically significant. In this regard, the suspend module has functionality 331 that can be manually set by a notification system operator to activate or to deactivate the suspend module functionality 330, and it has a clinically significant event duration setting 332 that can be programmed to define a minimum period of time (duration) that an clinical event should be active in order to be considered a clinically significant event for which an alarm is generated. So, in the event that the suspend functionality 330 is set to be active, and if an event is detected to be active for a period of time that is greater than that programmed in the event duration setting 332, then this event will cause an alarm to be generated and sent to a clinician, otherwise, no alarm will be generated.

Continuing to refer to FIG. 3, the call point object 300 has an event count function 340 that generally operates to count each instance of a short duration event that is detected by the event detection function 320 over a selected period of time The count function 340 receives an event message from the event detection function 320 each time a short duration event is detected, and increments an event count value that is maintained in a current count 341 store/register. The count function 340 continues to increment the current count 341 for a period of time that is selected by an operator and stored in a register associated with a count period timer 342, up to a count threshold value stored in a count threshold value register 343. If, prior to the value set on count period timer 342 being reached (prior to the timer expiring or timing out), the current count value stored in 341 is determined (by the logic 330) to be equal to or greater than the count threshold value stored in the register 343, than the alarm generation logic 330 overrides the suspend function 330 and causes an alarm to be immediately generated and sent to a clinician. Otherwise, if the count period times out before a current count value is determined to be equal to or greater than the count threshold, the current count 341 is reset to zero and no alarm is generated.

Figure 4A:
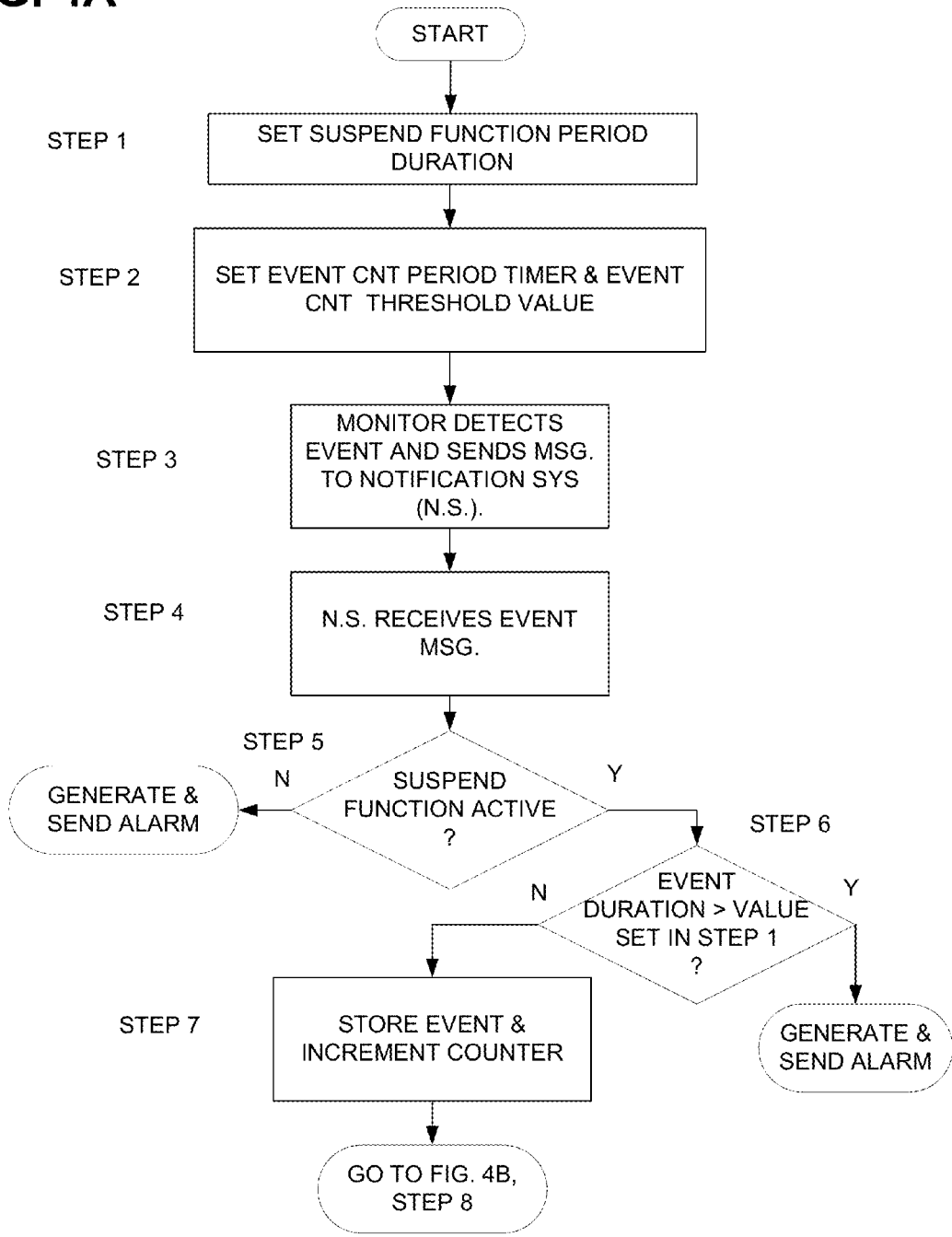
FIG. 4A is a logical flow diagram of an embodiment of the invention.
Figure 4B:
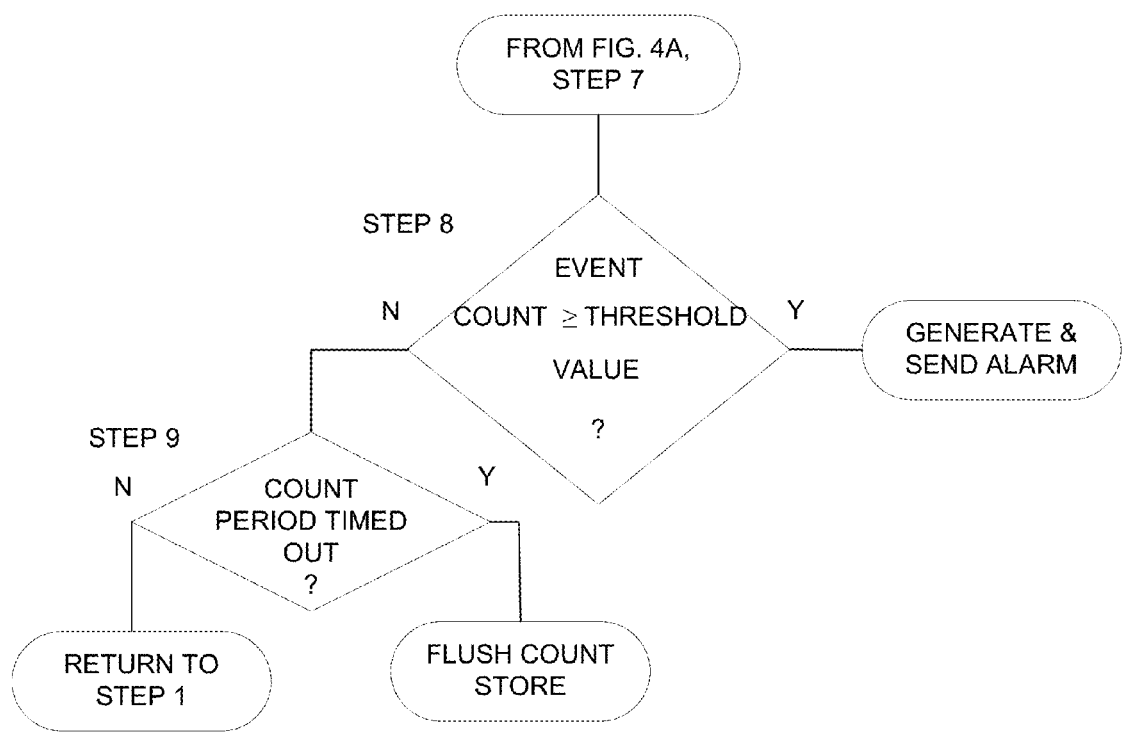
FIG. 4B is a continuation of the flow diagram of FIG. 4A.

The operation of the notification system 110 in the network 100 to detect and only report clinically significant events will now be described with reference to FIGS. 4A and 4B. In Step 1, a notification system operator sets/selects a value for the event duration setting 332, and in Step 2 sets a value for the count period timer 342 and the count threshold 343. The clinically significant event duration value 332 can be some number of seconds or minutes depending upon the monitored physiological characteristic and depending upon a clinicians previous experience in setting the value so that most or all clinically significant events are detected. The setting in Step 2 can also be selected by a clinician based upon the monitored physiological characteristic and previous clinical experience. In Step 3, any one of the patient monitors connected to the network 100 can detect an event and send an event message to the notification system 110 that, among other things, includes information indicative of a monitored physiological characteristic. In Step 4, the notification system 110 receives the event message and parses the information in the message (start time, stop time, physiological characteristic info). In Step 5, the notification function logic 350 determines whether the suspend function 330 is active or inactive (331), and if it is inactive the logical process proceeds to Step 5 and causes an alarm message to be generated and sent out, otherwise, the process proceeds to Step 6. In Step 6, the logic 350 determines (using the clinically significant event duration value set in 332 and information received from the even detection function 320) whether the event duration (time that the clinical event is active) is greater than the value set in Step 2, and if so an alarm is generated and sent out. On the other hand, if in Step 6 the event duration is determined to be less than the value set in Step 2, then the event count 341 is incremented by one and the process proceeds to Step 8 (FIG. 4B). If in Step 8 the logic 350 determines that the value currently stored in the current count 341 is greater that a threshold value set in 343, than an alarm is generated and sent out, otherwise the logic proceeds to Step 9 where it determines whether or not the value set in the count period duration 342 has timed out. If in Step 9 the count period has timed out, then the current value of the count stored in 341 is either flushed/deleted from memory/register or is in some other manner simply ignored, otherwise the logical process then returns to Step 1.

The forgoing description, for purposes of explanation, used specific nomenclature to provide a thorough understanding of the invention. However, it will be apparent to one skilled in the art that specific details are not required in order to practice the invention. Thus, the forgoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

We claim:

1. A method for identifying a clinically significant event, comprising:
    setting a value in a virtual call point for each of a clinically significant event duration, a clinical event count period and a clinical event count threshold;
    receiving at the virtual call point a plurality of clinical events associated with a patient the duration of at least some of which are detected to be less than the value set for the clinically significant event duration, and maintaining a current count of the clinical events having a duration that is less than the value set for the clinically significant event duration; and
    determining that the current count of clinical events having a duration that is less than the value set for the clinically significant event duration is equal to the count threshold value prior to the event count period expiring and determining that the patient is experiencing a clinically significant event.

2. The method of claim 1, further comprising the virtual call point deactivating an alarm suspend function that when active operates to prevent the generation of an alarm when the virtual call point detects a clinical event having a duration that is less than the value set for the clinically significant event duration.

3. The method of claim 2, further comprising the virtual call point generating and sending an alarm to a clinician that includes an indication that the patient is experiencing a clinically significant event.

4. The method of claim 1, wherein the clinically significant event duration value defines a minimum period of time that a clinical event is active to be considered clinically significant.

5. The method of claim 1, wherein the event duration value and the clinical event count period value is a predetermined period of time.

6. The method of claim 1, wherein the clinical event count threshold value is an integer value.

7. The method of claim 1, wherein the virtual call point is comprised of one or more virtual call point instances.

8. The method of claim 7, wherein each of the one or more virtual call point instances is comprised of a clinical event detection function, an alarm suspend function, a clinical event counting function and an alarm generation function.

9. The method of claim 1, wherein each one of the plurality of clinical events is received from a patient monitoring device and is comprised of clinical event information relating to the physiological state of a patient.

10. The method of claim 9, wherein the clinical event information is any one or more of a heart rate, blood pressure, respiratory rate, blood oxygen, and body temperature.

11. An event notification system, comprising:
a virtual call point having a clinical event detector, a clinical event counter, and alarm generation logic;
wherein the virtual call point receives a plurality of clinical events associated with a patient, the clinical event detector determining that a least some of the clinical events having a duration that is less than a pre-set clinically significant event duration are not clinically significant and the clinical event counter maintaining a current count of the events that are not clinically significant; and
the alarm generation logic detecting that the current count of clinical events that are not clinically significant is equal to a clinical event threshold value prior to a clinical event count period expiring and determining that the patient is experiencing a clinically significant event.

12. The event notification system of claim 11, further comprising an alarm suspension function that when active operates to prevent the generation of an alarm when the virtual call point detects a clinical event that is not clinically significant.

13. The event notification system of claim 12, further comprising the virtual call point deactivating the alarm suspension function and sending an alarm to a clinician indicating that a clinically significant event is detected.

14. The event notification system of claim 12, wherein the alarm suspension function comprises a clinically significant event duration threshold that is set to a value that defines a minimum period of time that a clinical event is active to be considered clinically significant.

15. The event notification system of claim 14, wherein the value that defines a minimum period of time that a clinical event is active is a predetermined period of time.

16. The event notification system of claim 11, wherein the clinical event threshold value is an integer value.

17. The event notification system of claim 11, wherein the clinical event count period is set to a predetermined period of time value.

* * * * *